United States Patent
Klingbeil et al.

(10) Patent No.: US 11,478,312 B2
(45) Date of Patent: Oct. 25, 2022

(54) UNMATCHING/MATCHING UID TO ROBOT GRASPER FOR ENGAGING TELEOPERATION

(71) Applicant: Verb Surgical Inc., Mountain View, CA (US)

(72) Inventors: Ellen Klingbeil, Mountain View, CA (US); Haoran Yu, Milpitas, CA (US)

(73) Assignee: VERB SURGICAL INC., Santa Clara, CA (US)

(*) Notice: Subject to any disclaimer, the term of this patent is extended or adjusted under 35 U.S.C. 154(b) by 664 days.

(21) Appl. No.: 16/409,620

(22) Filed: May 10, 2019

(65) Prior Publication Data
US 2020/0352663 A1 Nov. 12, 2020

(51) Int. Cl.
- A61B 34/35 (2016.01)
- A61B 17/28 (2006.01)
- G16H 40/67 (2018.01)
- A61B 34/00 (2016.01)
- A61B 17/00 (2006.01)

(52) U.S. Cl.
CPC .............. *A61B 34/35* (2016.02); *A61B 17/28* (2013.01); *G16H 40/67* (2018.01); *A61B 2017/00199* (2013.01); *A61B 2017/00216* (2013.01); *A61B 2017/00973* (2013.01); *A61B 2034/252* (2016.02)

(58) Field of Classification Search
CPC ................. A61B 34/35; A61B 17/28; A61B 2017/00199; A61B 2017/00216; A61B 2017/00973; A61B 2034/252; A61B 2017/00424; G16H 40/67
See application file for complete search history.

(56) References Cited

U.S. PATENT DOCUMENTS

| | | | |
|---|---|---|---|
| 6,587,750 B2 * | 7/2003 | Gerbi | A61B 34/71 600/595 |
| 6,879,880 B2 * | 4/2005 | Nowlin | A61B 34/70 318/568.22 |
| 2017/0042625 A1 | 2/2017 | Sartor | |
| 2017/0319284 A1 | 11/2017 | Itkowitz et al. | |
| 2018/0161108 A1 | 6/2018 | Savall et al. | |
| 2018/0296286 A1 | 10/2018 | Peine et al. | |

FOREIGN PATENT DOCUMENTS

WO 2018162921 9/2018

OTHER PUBLICATIONS

International Search Report and Written Opinion for International Application No. PCT/US2019/032049 dated Feb. 6, 2020, 10 pages.
International Preliminary Report on Patentability for International Application No. PCT/US2019/032049 dated Nov. 25, 2021, 6 pages.

* cited by examiner

*Primary Examiner* — Julian W Woo
(74) *Attorney, Agent, or Firm* — Womble Bond Dickinson (US) LLP (57) ABSTRACT

A surgical robotic system has a robotic grasper, a user interface device (UID), and one or more processors communicatively coupled to the UID and the robotic grasper. The system detects a directive to engage or re-engage a teleoperation mode, determines that the system is in a non-teleoperation mode, receives a sequence of user actions through the UID, determines the UID matches a jaw angle or a grip force of the robotic grasper, and transitions into teleoperation mode. Other embodiments are also described and claimed.

20 Claims, 8 Drawing Sheets

UNMATCHING/MATCHING UID TO ROBOT GRASPER FOR ENGAGING TELEOPERATION

An embodiment of the invention relates to user input devices, robot or robotic graspers, and teleoperation of the robotic graspers. Other embodiments are also described.

BACKGROUND

In a surgical robotic system, a robotic arm that has a surgical tool attached to its distal end is remotely operated by a surgeon—this is also referred to as teleoperation. Applications include endoscopic surgery, which involves looking into a patient's body and performing surgery inside, for example the abdominal cavity, using endoscopes and other surgical tools that are attached to the ends of several robotic arms. The system gives the surgeon a close-up view of the surgery site while at the same enabling the surgeon to remotely operate the tool that is attached to the arm by manipulating a handheld user interface device (UID), all in real-time. The tool may be a gripper with jaws, a cutter, a video camera, or an energy emitter such as a laser used for coagulation. The tool is thus controlled by the system, in a precise manner and with high dexterity, in accordance with the surgeon manipulating a handheld UID.

The core function of a UID is to act as an input device to control the translation, rotation and other actions such as grasping, of end effectors of surgical tools. One type of tool is the grasper, which has two jaws controlled by the open and close movements of a UID's grip linkage or deformable surface that can be squeezed or pressed to close the jaws. Other UIDs have other types of linkages or mechanisms.

SUMMARY

Various aspects of a surgical robotic system that performs a method for engaging a user interface device (UID) to a surgical robotic grasper for teleoperation are described herein. These embodiments assist in solving a problem of when and how to initially engage teleoperation at the start of a surgical session, and also a problem of when and how to re-engage teleoperation from a paused mode or from a disengaged mode (where the system became paused or disengaged during teleoperation in an on-going surgical session), so as to decrease risks of the robotic grasper damaging the patient's tissue, damaging equipment or inadvertently releasing tissue during surgery. The UID has a grasper part such as a linkage, a deformable surface that can be squeezed or pressed, or other finger actuated mechanism whose position or orientation is sensed as an electronic user input signal (user input). When teleoperation is engaged, the user input is processed by a control system to, in a general sense, proportionally control the angle and/or force of a surgical robotic grasper during teleoperation.

In one embodiment, the surgical robotic system has a robotic grasper with two jaws, a user interface device (UID) with a grasper part for which a sensed signal (user input) is generated by sensing electronics, and one or more processors (generically referred to here as "a processor" for convenience) that are communicatively coupled to the UID sensing electronics and the robotic grasper. The processor is configured to perform a process that decides when it is permissible to engage or re-engage a teleoperation mode in which the robotic grasper is controlled by user input from the UID.

In one embodiment, the processor may first determine that the surgical robotic system is in a non-teleoperation mode (e.g., a paused or "clutched" mode, a disengaged mode, or waiting for teleoperation to be initiated at the start of a surgical session). The processor receives a sequence of detected user actions through the UID (also referred to here as user input). The processor determines based on the received user input when the UID (its grasper part) matches i) a jaw angle of the robotic grasper (an angle between the two jaws of the robotic grasper), or ii) a grip force affected by the two jaws of the robotic grasper. The processor transitions the surgical robotic system into teleoperation mode, responsive to the determination that the UID matches the jaw angle or the grip force of the robotic grasper.

In another embodiment, the surgical robotic system performs a method of re-engaging teleoperation, as follows. First, a processor of the system determines that the surgical robotic system, during teleoperation, has transitioned to a disengaged mode, and in response starts to execute a finite state machine having multiple states. While executing the state machine, the processor receives a sequence of detected user actions (user inputs) which include user finger actuations of the grasper part of the UID. This sequence of detected user inputs is interpreted by the system, causing the state machine to transition between several states of a so-called unmatch/match algorithm. When the state machine reaches a state of that algorithm corresponding to the UID user input matching a jaw angle or a grip force of the robotic grasper, the surgical robotic system re-engages in teleoperation of the robotic grasper.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Several embodiments of the invention with reference to the appended drawings are now explained. Whenever the shapes, relative positions and other aspects of the parts described in the embodiments are not explicitly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

A surgical robotic system and algorithm described herein ensure that teleoperation is not engaged unless the interface device (UID) matches the surgical robotic grasper, in terms of jaw angle and/or grip force of the surgical robotic grasper. In one embodiment, if teleoperation is being re-engaged from a disengaged (inactive) mode, a mismatch (or "unmatch") between the UID and robot grasper must first be deliberately formed (via user actions on the finger actuated UID grasper), before matching. In contrast, when seeking to re-engage teleoperation from a paused mode (also referred to as a clutched mode, where the control system had frozen the robotic grasper in response to the user actuating a pause or clutch button in the UID or the user initiating another form of pause or clutch command), the algorithm need not look for an initial unmatch and instead can allow re-engagement of teleoperation when it detects that the UID user input matches the held, jaw angle and/or grip force of the surgical robotic grasper.

Figure 1:
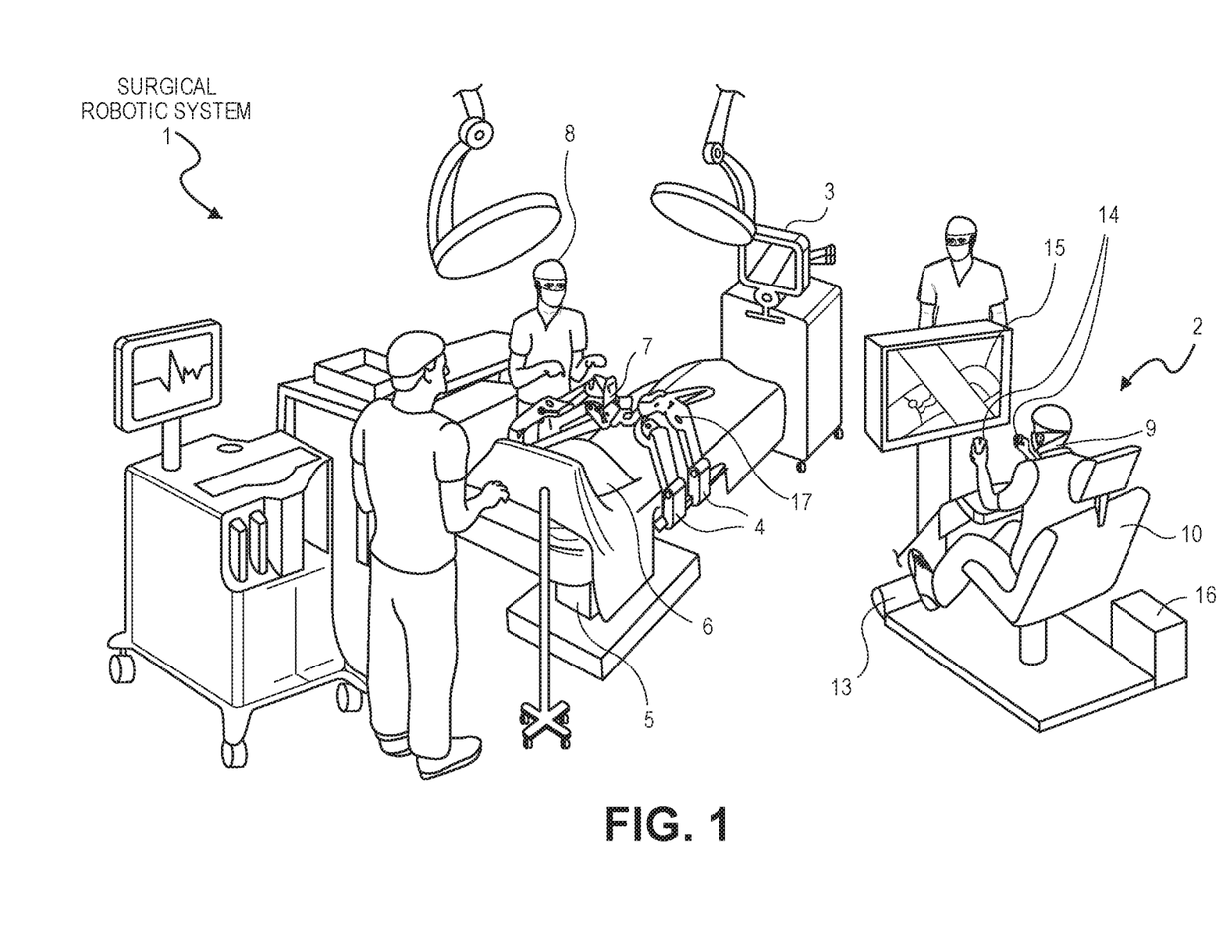
FIG. 1 is a pictorial view of an example surgical robotic system in an operating arena.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4).

In some embodiments, UID 14 may be a portable handheld user input device or controller that is ungrounded with respect to another component of the surgical robotic system. For example, UID 14 may be ungrounded while either tethered or untethered from the user console 2. The term "ungrounded" is intended to refer to implementations where, for example, one or more UIDs are neither mechanically nor kinematic ally constrained with respect to the user console 2. For example, a user may hold a UID 14 in a hand and move freely to any possible position and orientation within space only limited by, for example, a tracking mechanism of the user console." In contrast, a grounded UID can hold its position/orientation/gripping.

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site). Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

One problem to be solved in a surgical robotic system 1 is how or when to engage or resume (i.e., re-engage) teleoperation safely, without causing unintended movements of surgical tools that may lead to tissue damage. Without the solution described herein, there is a risk that re-engaging teleoperation, in particular when teleoperation was interrupted for some reason (the system entered a disengaged mode), could result in a surgical robotic grasper to suddenly open, suddenly close, clamp down too hard on tissue or release tissue that had been previously grasped, etc.

The present system determines when user input from a user interface device (UID) matches a grasper angle or grasper force of a surgical robotic grasper, at which point teleoperation of the robotic grasper may be engaged. The UID is not mechanically constrained to maintain the same position, orientation, and grasper angle or force as the surgical tool. Accordingly, an algorithm is described that, when performed, detects when the grasper part of the UID is matching the surgical tool grasper (with respect to angle and force, i.e., the UID and the surgical robotic grasper are within an acceptable threshold of agreeing with each other) before the system engages or resumes (i.e., re-engages) teleoperation. This algorithm may be especially useful for an ungrounded UID, which does not hold its position or orientation when released by a user. Two devices that are matched, in this context, means that the positions and orientations or other relevant values of the two devices are within a threshold of agreement with each other. The process of matching means the process of bringing the positions and orientations or other relevant values of the two devices to within a threshold of agreement with each other. User input from the grasper part of a UID is translated to an angle and grasping force for the surgical robotic grasper. The system in one embodiment first looks for the case where the UID and the robotic grasper do not yet match (e.g., the system waits until the user input from the UID has changed enough to be outside the threshold of agreement with the current angle and/or force of the robotic grasper). Sometime thereafter the user's finger manipulation of the UID results in the user input matching the currently stationary angle and/or force of the surgical grasper. Upon detecting this match, the system may respond with an alert to the user and with engaging teleoperation of the surgical robotic grasper.

In one embodiment, the user is expected to open the UID, past a UID open threshold, or start with the UID in an open position or orientation. For example, the user can set a grip crank of the UID to an angle greater than a UID open threshold. Then the user closes the UID. For example, the user can close the UID past a UID closed threshold. During this time, the algorithm is monitoring the user input which reflects the change of the grasper part of the UID from open to close. After having closed the grasper part of the UID, the user opens it, while the algorithm is still monitoring the user input, until the algorithm determines that the user input matches the surgical grasper, in response to which teleoperation is engaged. Matching the UID to the tool grasper before engaging teleoperation helps to prevent damage to the surgical tool and the tissue. Requiring a mismatch, by first opening and closing the UID, and then a match of the UID to the surgical robotic grasper, removes guess work and thus helps ensure safe transition from a disengaged mode (in which teleoperation of the robotic grasper is disabled) to the teleoperation enabled mode (see FIG. 5A).

Figure 2A:
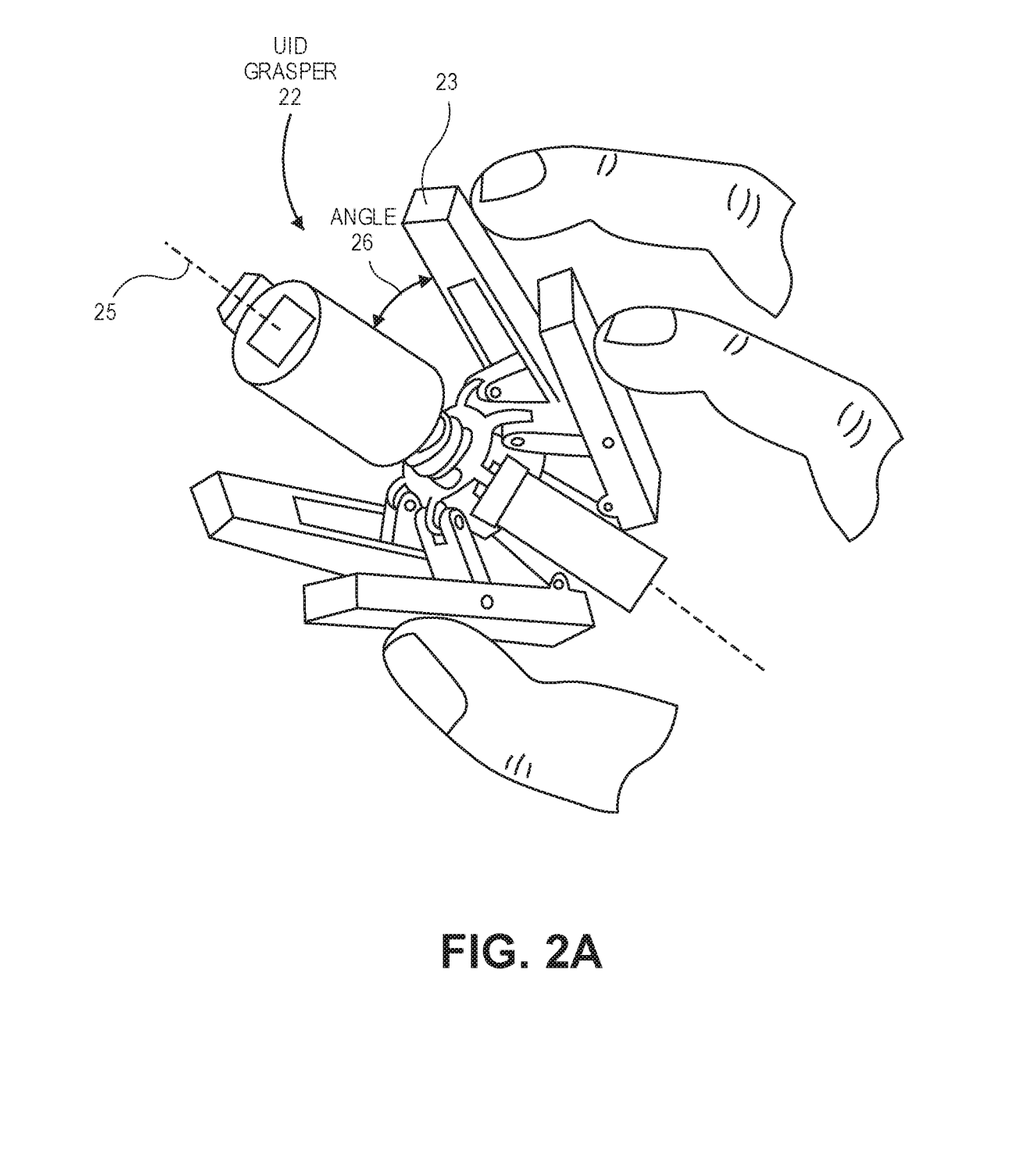
FIG. 2A illustrates an example of a user input device (UID).

FIG. 2A illustrates an example of a UID grasper part (UID grasper 22) which may be part of the UID 14—see FIG. 1. The UID grasper 22 has one or more moveable grip cranks 23 and associated electronic circuitry (not shown) that can sense the position of the grip crank 23. The UID grasper 22 as part of the UID 14 is being held in a user's hand in an open configuration, with its grip cranks 23 in a fully open position as shown. The UID grasper 22 is designed to enable the user's finger to manipulate the grip crank 23 across its range of position (angle 26, between grip crank 23 and axis 25) by a finger squeeze action, which position is sensed by the associated electronic circuitry and then translated by a controller 39 (see FIG. 3) into a corresponding position (angle) command for actuating a jaw of the grasper of the surgical tool 7. The user's hand can manipulate the UID grasper 22 in various ways. Furthermore, the grip cranks 23 can provide tactile feedback to the user or surgeon when the user's hand pinches or squeezes the grip cranks 23 inward toward axis 25, to reduce the angle 26 (i.e., "closing" the UID 14.) Accordingly, such a UID 14 provides enhanced dexterity and precision of movement for controlling a surgical robotics tool. Other UIDs can be used in further embodiments of the surgical robotic system, including for example one whose UID grasper 22 is different than the version shown in FIG. 2A.

Figure 2B:
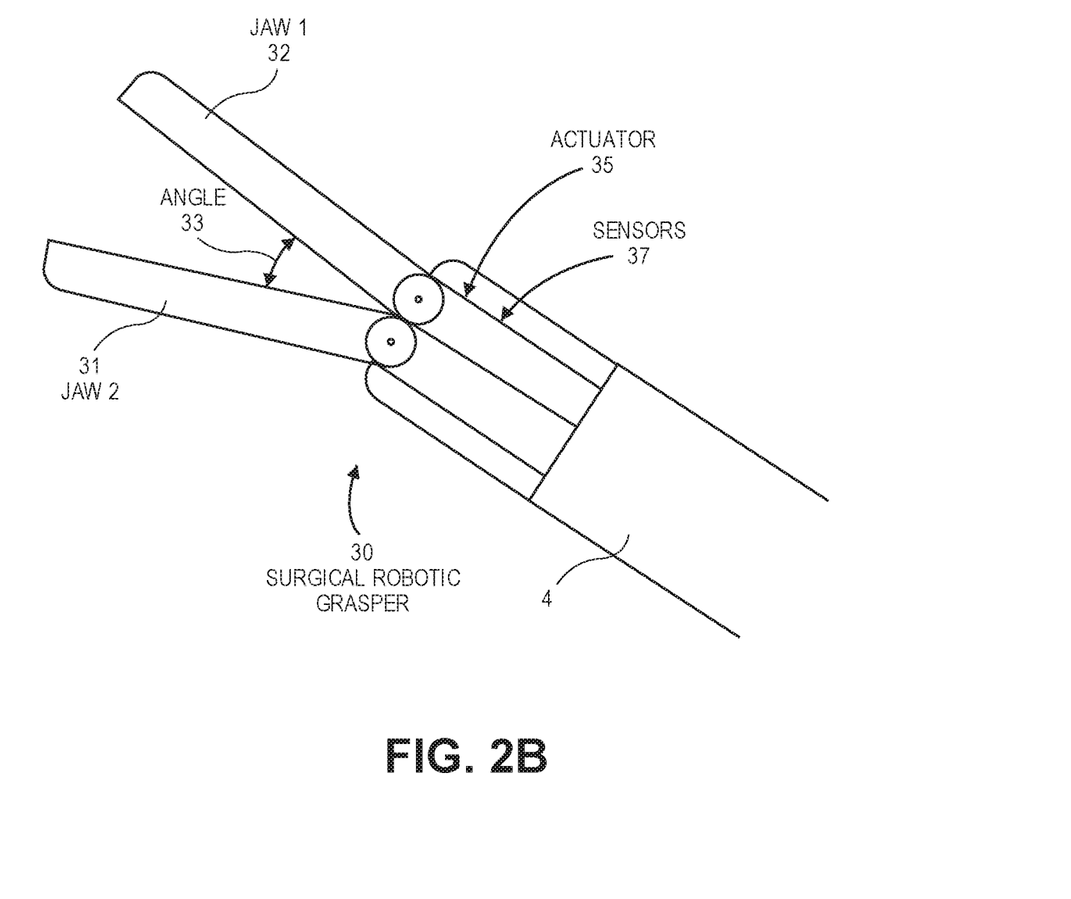
FIG. 2B illustrates an example of a surgical robotic grasper attached to a surgical robotic arm.

FIG. 2B illustrates an example of a surgical robotic grasper 30, attached to a surgical robotic arm 4. Two jaws 31, 32, labeled jaw 2 and jaw 1, are moved by an actuator 35 through an angle 33 between the two jaws 31, 32, that is sensed by sensors 37. In a surgical robotic system, the jaws 31, 32 are used to grasp tissue, and the angle 33 is controlled by driving the actuator 35 based on measurement by the sensors 37. Sensors 37 also measure the force of the grip exerted by the jaws 31, 32. Other surgical robotic graspers or end effectors and tools can be used in further embodiments of the surgical robotic system.

Figure 3:
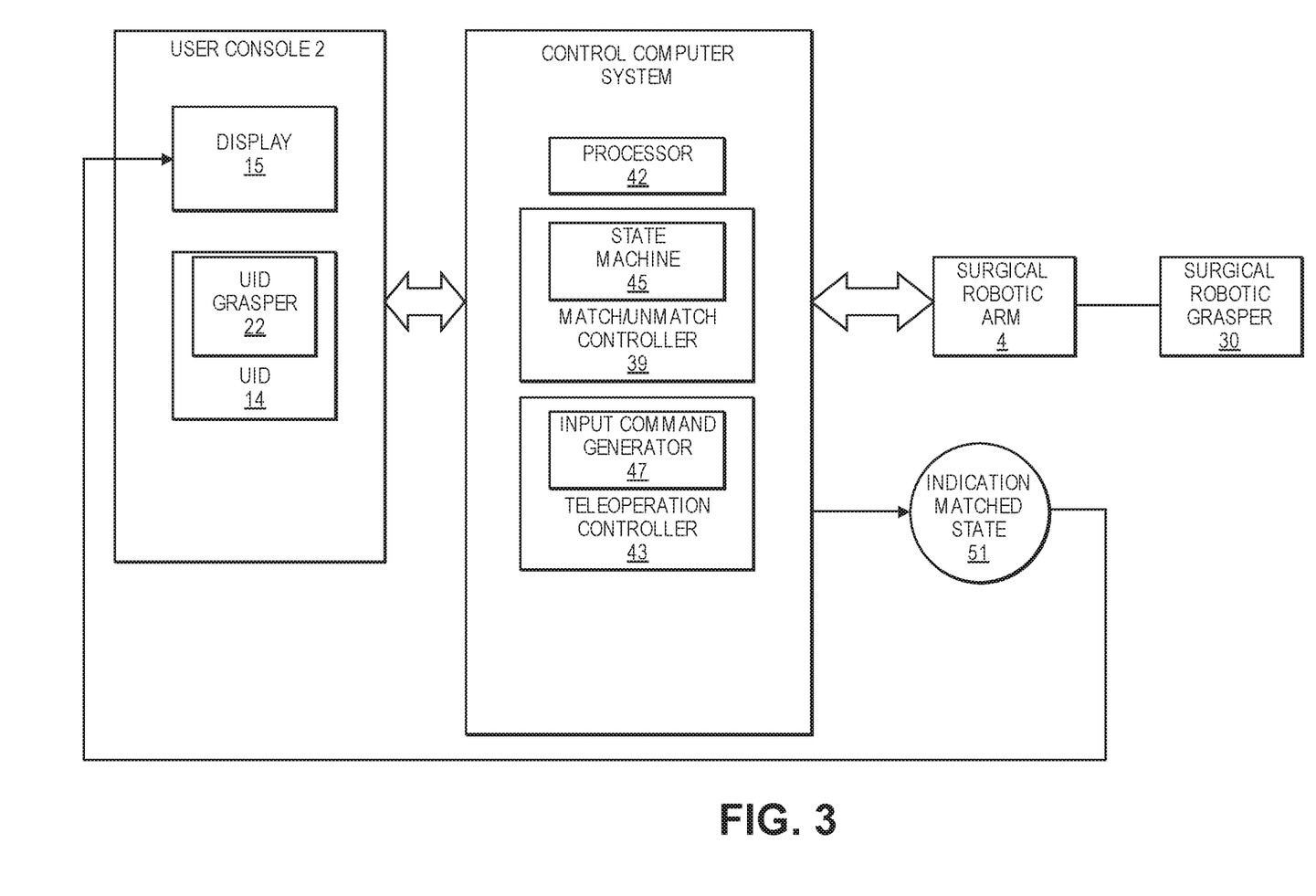
FIG. 3 is a block diagram of a surgical robotic system with a UID, surgical robotic arm, surgical robotic grasper and control computer system, for implementing teleoperation with the UID matched to the surgical robotic grasper.

FIG. 3 is a block diagram of a surgical robotic system that includes the UID 14 (having the UID grasper 22), surgical robotic arm 4, surgical robotic grasper 30 and a computer system for implementing teleoperation with the UID matched to the surgical robotic grasper. The computer system has one or more processors (processor 42) which executes software (stored in memory). These include a match/unmatch controller 39 which includes a state machine 45. In addition, a teleoperation controller 43 controls teleoperation of the surgical robotic arm 4 and surgical robotic grasper 30 in accordance with user input from the UID 14. The teleoperation controller 43 has an input command generator 47 that translates or converts sensor measurements of the UID 14 (including translation, rotation and grasping) into input commands for the teleoperation of the surgical robotic arm 4 and surgical robotic grasper 30. The computer system shown in FIG. 3 may be implemented as part of the control tower 3—see FIG. 1.

In some implementations, the UID grasper 22 includes a grip linkage or a deformable surface, and one or more sensors as part of the user console 2 that generate grasp signals as the user input that controls the jaw angle and grip force of the robotic grasper 30 (in accordance with user actions such as squeezing of the grip linkage or the deformable surface). These grasp signals are examples of detected user actions. For example, the grasp signals may include sensor measurement of angle 26 (or degree of deformation of the UID surface) caused by the user's finger actuation of the grip linkage or deformable surface. The grasp signals are input to the control computer system to generate control commands, which cause the two jaws of the robotic grasper to close/open at a certain jaw angle and/or affect a certain force. A purpose of the match/unmatch process is that when the user squeezes the grip linkage or deformable surface, the sensor measurements (and thus the grasp signals) will at that point correspond to, i.e., are matching the, current jaw angle and force of the robotic grasper. As a result, when the robotic system is, at that point, engaged/re-engaged into teleoperation, the robotic grasp will maintain the same jaw angle and grip force as it had when it was disengaged or paused, without any sudden movements.

The match/unmatch process may be performed by the processor 42 executing the state machine 45 (as software). Functions of the state machine 45 are discussed in more detail below with reference to FIG. 5A and FIG. 5B. More generally, the state machine 45 keeps track of a teleoperation mode and an unmatched/matched state, of the UID and surgical robotic grasper 30. It outputs an indication 51 of a matched state, when (or in response to) the user input from the UID matching the angle and/or force of the surgical robotic grasper. This indication 51 could be presented to a user in the form of an audio message, such as a tone, sound or speech, a visual alert such as a light turning on or flashing, a text or graphic message displaying on a display 15 of the user console 2, a tactile alert such as vibration, for example of the UID 14, an armrest or a seat vibrator in the user console 2, or other notification to the user at the user console 2. Or, the indication 51 could trigger the engagement of teleoperation, with or without a further notification, in various embodiments.

Figure 4A:
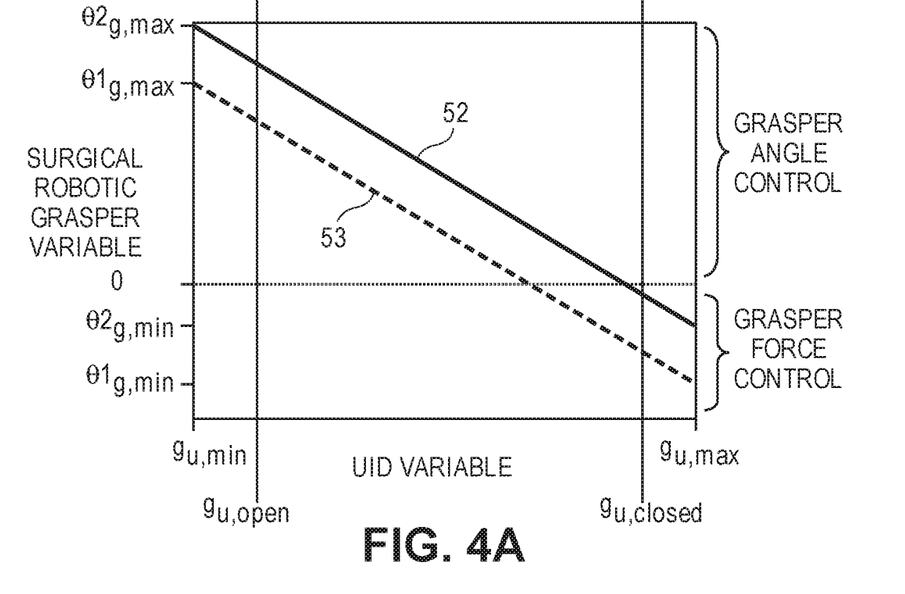
FIG. 4A is a graph of an example mapping from UID value (user input) to surgical robotic grasper angle and force, for two different tools.

FIG. 4A is a graph for translating from UID user input value to a surgical robotic grasper control command, the latter being a value that specifies a surgical robotic grasper angle and/or force. The graphs for two different tools are shown, graphs 52, 53. The UID status (e.g., open, closed, matched to robotic grasper, or not matched to robotic grasper) can be derived from analysis of the UID value and analysis of the sensed surgical robotic grasper angle and force. During teleoperation, the UID is presumed to continually match the surgical robotic grasper (due to the control system at work), which means that the measured pair, (UID value, robotic grasper value), at any given moment defines a point that is on or within a threshold band around the graph 52 (for that particular tool). But when the measured pair defines a point that is not within the threshold band around the graph 52, the UID and the robotic grasper are said to be unmatched. The latter should only occur during a non-teleoperation mode.

The graph 52 describes a linear relationship between the UID value (angle) on the x-axis, and angle of the surgical robotic grasper on the y-axis. The graph 52 extends from grasper angle control through grasper force control over a range of minimum to maximum angle of the UID, and minimum to maximum angle of the surgical robotic grasper. Generally, a portion of the x-axis (UID variable) translates to grasper angle, and another portion of the UID variable translates to grasper force, as shown. The UID is considered open when the UID value is less than or equal to $g_{u,open}$, and thus within a guard band threshold of $g_{u,min}$. At the opposite end of the range, the UID is considered closed when the UID value is greater than or equal to $g_{u,closed}$, and thus within a guard band threshold of $g_{u,max}$. Another graph 53 (in dashed line) for another tool shows a similar linear relationship between angle of the UID and angle of the surgical robotic grasper, but shifted through a different range of minimum to maximum angle of the surgical robotic grasper. Other graphs, including ones having curved or segmented relationships among angles and force for various tools are readily developed and understood in keeping with the teachings herein.

Figure 4B:
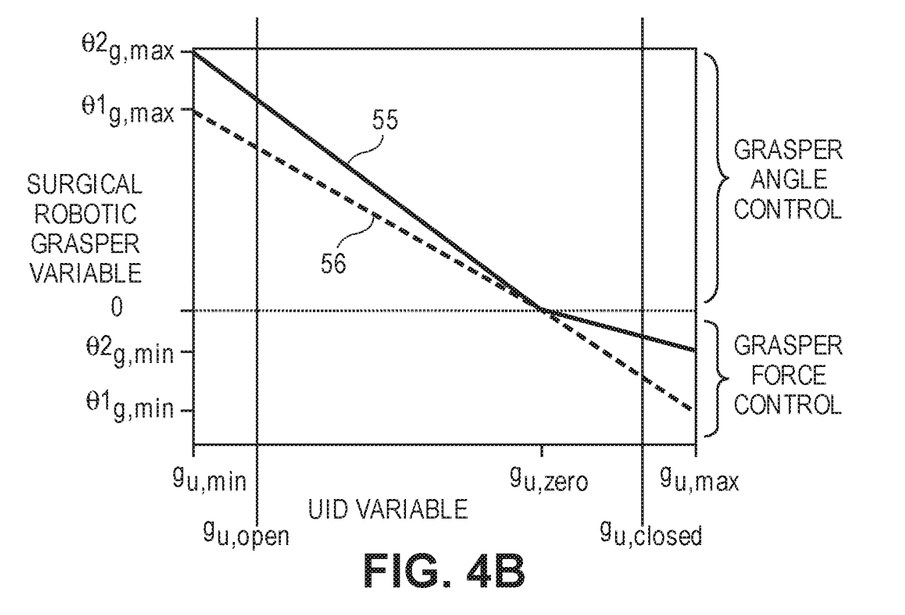
FIG. 4B is a graph of another example mapping from UID value to surgical robotic grasper angle and force, for two different tools.

FIG. 4B is a graph for mapping from UID value to surgical robotic grasper angle and force, for two different tools in a further embodiment. One graph 55 (in solid line) for one tool shows a linear relationship between value (in this case, measurement of an angle) of the UID and angle of the surgical robotic grasper for grasper angle control, transitioning to a different slope for grasper force control. Another graph 56 (in dashed line) for another tool shows a linear relationship between value (angle) of the UID and angle of the surgical robotic grasper extending without change in slope from grasper angle control through grasper force control. Both graphs 55, 56 transition from grasper angle control to grasper force control at the same angle of the UID (e.g., zero). Other graphs, including showing other transition points, other slopes, and other relationships among angles and force for various tools are readily developed and understood.

The unmatch/match algorithm may consist of a state machine that requires the UID to transition through a series of states, in order to unmatch and then match the UID to the robot grasper, before engaging teleoperation from a disengaged (inactive) mode. In one embodiment, when engaging teleoperation from a paused mode (rather than a disengaged or inactive mode), the algorithm does not require detection of a particular unmatch condition, and instead directly looks for a match condition; in other words, a determination that the UID and the robot grasper first be unmatched is not needed in that case.

The robot grasper is represented by an opening angle and a grasping force, which will be denoted as $g_r = [\theta_g f_g]$. The UID value, denoted as $g_u$, is represented using a range of numerical values. During teleoperation, a UID input is translated to an opening angle and grasping force (control command) for the robot grasper, for example in accordance with the graphs shown in FIGS. 4A and 4B, and variations thereof. The function that translates UID value to robot grasper value will be represented as: $g_r = f(g_u)$. The lower and upper numerical limits for the UID grasper value are given by $g_{u,min}$ and $g_{u,max}$, respectively. The lower limit $g_{u,min}$ corresponds to the position where the UID is fully open, and the upper limit $g_{u,max}$ corresponds to the position where the UID is fully closed. As to the robot grasper angle, its lower and upper limits are given by $\theta_{g,min}$ and $\theta_{g,max}$, respectively. The robot grasper force is bounded by $(0, f_{g,max})$. The function $f$ translates UID fully open to robot grasper maximum opening angle and zero force. The UID fully closed is translated to the robot grasper applying maximum force, which can occur across the range of robot grasper opening angles, depending on the width of the tissue being grasped.

The robot grasper value that is to be compared to the present UID value by the unmatch/match algorithm may be calculated using the inverse mapping: $\tilde{g}_r = f^{-1}(g_r)$. The inverse function converts the current robot grasper angle and force to UID units, so the UID and robot grasper values can be compared in consistent units by the unmatch/match algorithm. The inverse translation is represented by the following equations:

$$\bar{\theta}_g = \{\max(\theta_{g,min}, \min(\theta_g, \theta_{g,max}))\},$$

$$f_g \leq \varepsilon_f \min\left(\left(\frac{f_g}{k_{angle\_to\_force}}, \frac{f_{g,max}}{k_{angle\_to\_force}}\right)\right), f_g > \varepsilon_f$$

$$\alpha = \frac{g_{u,max} - g_{u,min}}{\theta_{g,max} - \theta_{g,min} - \frac{f_{g,max}}{k_{angle\_to\_force}}}$$

$$\tilde{g}_r =$$

$$\{g_{u,min} + \alpha(\theta_{g,max} - \bar{\theta}_g), \bar{\theta}_g \geq g_{u,min} + \alpha(\theta_{g,max} - \theta_{g,min} - \bar{\theta}_g), \bar{\theta}_g < 0$$

The parameter $k_{angle\_to\_force}$ is a negative valued parameter and the quantity $1/k_{angle\_to\_force}$ converts a force to a negative angle to translate both gripper angle and force to units of the UID. The variable $\alpha$ is the scaling between UID units and robot grasper angle. The parameter $\varepsilon_f > 0$ can be set based on the accuracy of estimating the measured gripper force.

Note that the above translation allows for minimum gripper angle to be greater than zero. Given that in most cases, the minimum gripper angle is zero, the equations can be simplified as below for this case.

$$\bar{\theta}_g = \{\max(\theta_{g,min}, \min(\theta_g, \theta_{g,max}))\},$$

$$f_g \leq \varepsilon_f \min\left(\left(\frac{f_g}{k_{angle\_to\_force}}, \frac{f_{g,max}}{k_{angle\_to\_force}}\right)\right), f_g > \varepsilon_f$$

$$\alpha = \frac{g_{u,max} - g_{u,min}}{\theta_{g,max} - \frac{f_{g,max}}{k_{angle\_to\_force}}}$$

$$\tilde{g}_r = g_{u,min} + \alpha(\theta_{g,max} - \bar{\theta}_g)$$

The unmatch/match algorithm may use three parameters that can be tuned according to the given UID and robot grasper properties. We define $g_{u,open}(\geq g_{u,min})$ as the gripper open threshold, and $g_{u,closed}(\leq g_{u,max})$ as the gripper closed threshold. The matching threshold is denoted as $\delta g_{match}$. The UID and robot grasper are considered to be "matching" if $|\tilde{g}_r - g_u| \leq \delta g_{match}$.

The unmatch/match algorithm may consist of the following four states:

| State description | State name |
|---|---|
| Waiting for UID grasper to open | UNMATCHING_OPEN |
| Waiting for UID grasper to close | UNMATCHING_CLOSE |
| Waiting for UID grasper to match surgical robotic grasper | MATCHING |
| UID grasper and surgical robotic grasper matched | MATCHED |

Figure 5A:
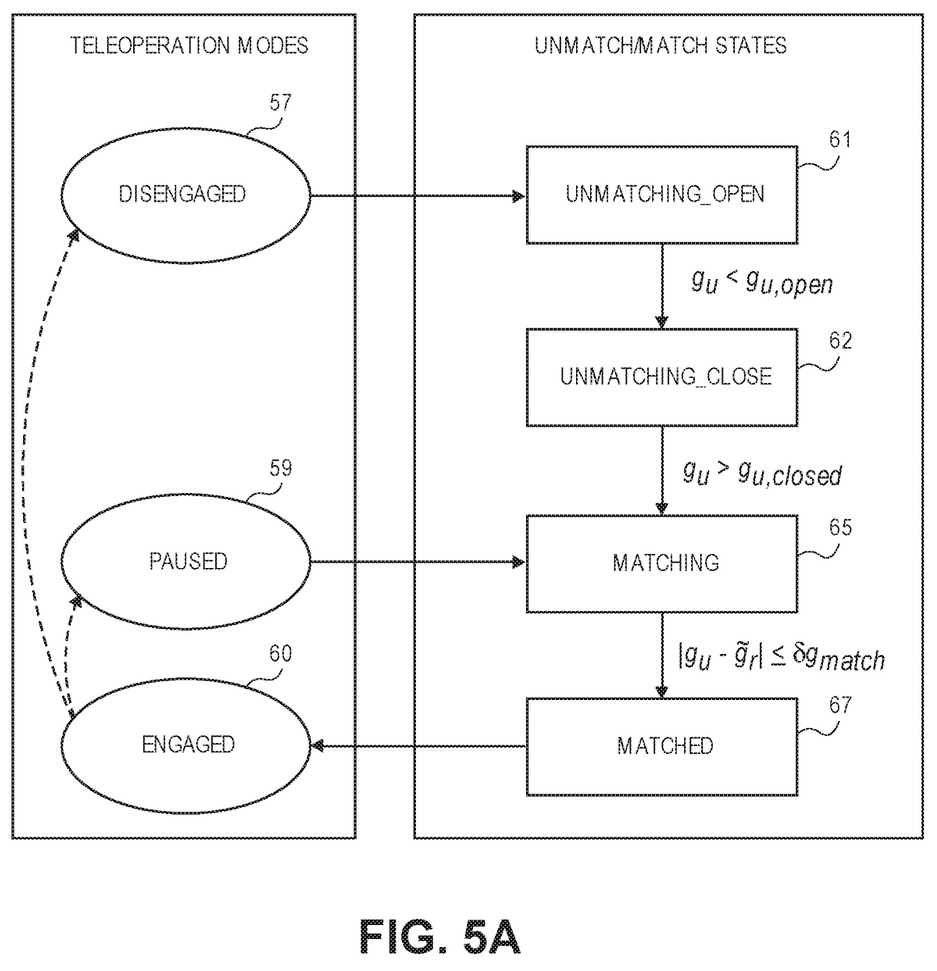
FIG. 5A is a state diagram for matching the UID to the surgical robotic grasper, in an embodiment.
Figure 5B:
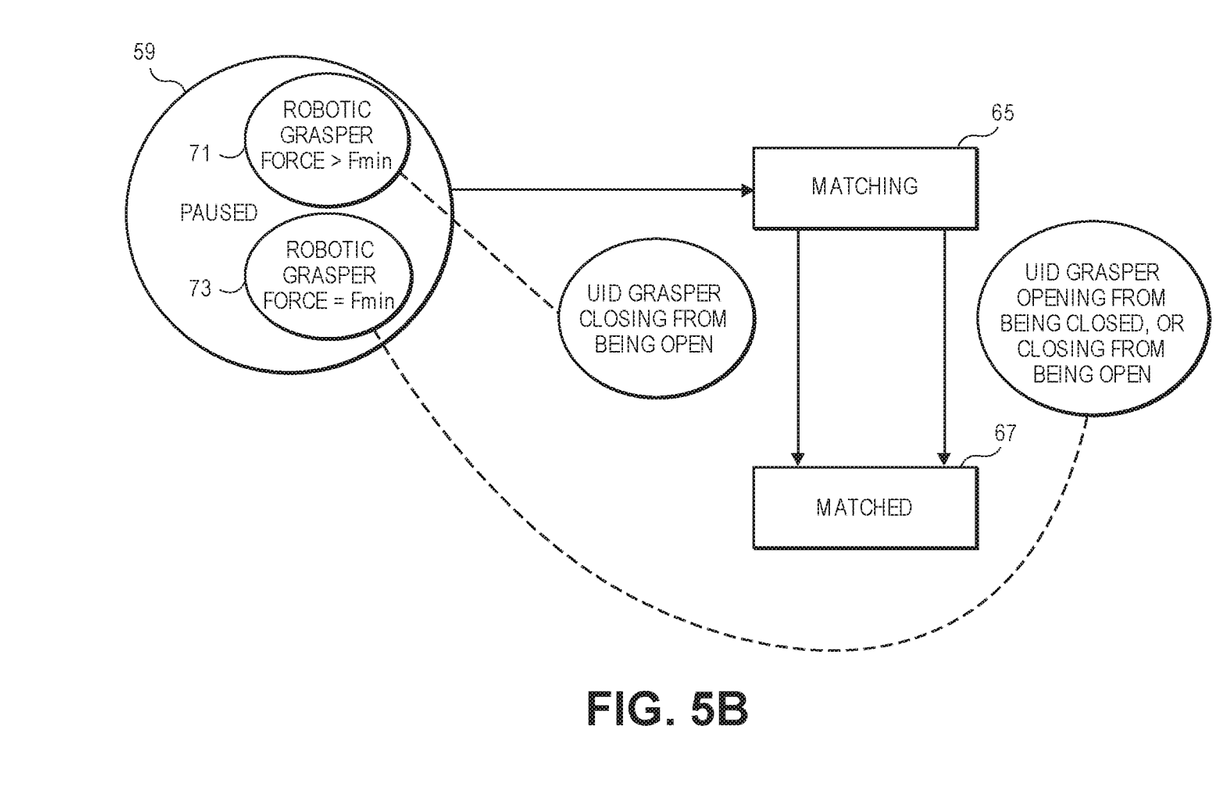
FIG. 5B is a further state diagram for matching the UID to the surgical robotic grasper, in a further embodiment.

The algorithm state machine logic is depicted in the diagrams of FIG. 5A and FIG. 5B. FIG. 5A is a diagram of various teleoperation modes and an algorithm for matching the UID to the surgical robotic grasper, in an embodiment. While FIGS. 4A and 4B show the correspondence of a range of UID value (in this case, angle) to surgical robotic grasper angle and force, with the UID matched to the surgical robotic grasper during teleoperation. In FIG. 5A the left column indicates the teleoperation modes of {DISENGAGED 57, PAUSED 59, ENGAGED 60}. The right column in FIG. 5A indicates the states of the unmatch/match algorithm {UNMATCHING_OPEN 61, UNMATCHING_CLOSE 62, MATCHING 65, MATCHED 67}. The arrows indicate allowable transitions between the states and modes. Note that FIG. 5A is not showing details of other operations that may be needed in order to transition between the teleoperation modes as those are not part of the unmatch/match algorithm proposed here. The teleoperation mode of DISENGAGED 57 directs the unmatching/match algorithm to the state of UNMATCHING_OPEN 61 (the system is waiting for the UID to open.) In response to the user opening the UID grasper 22, the algorithm transitions to the state of UNMATCHING_CLOSE 62 (the system is waiting for the UID to close). The user then closes the UID grasper 22, and the algorithm detects and responds to that by transitioning to MATCHING 65 (the system is waiting for UID to match the surgical robotic grasper). The user then opens the UID grasper 22 until the algorithm detects that the UID value (user input) agrees with the robotic grasper angle and/or force to within a threshold, and responds by making the transition from MATCHING 65 to MATCHED 67 (the system has determined that the UID and the surgical robotic grasper match). When the MATCHED 67 state is achieved, the teleoperation mode becomes ENGAGED 60. That is, teleoperation of the surgical robotic grasper 30 by the UID 14 is engaged, in response to determining that the UID is matching the surgical robotic grasper as indicated by the MATCHED 67 state.

FIG. 5B is a further state diagram for matching the UID to the surgical robotic grasper, in a further embodiment. While teleoperation is engaged, the user, for example a surgeon, may need to pause (or clutch) the surgical robotic system, for example in order to rest, observe the patient or progress of surgery, obtain additional surgical strategy or instructions, consult with other surgical personnel, etc. Pausing the surgical robotic system could be performed by voice command, interaction with a user interface, a button on the UID, or other controls, etc., any of which in various embodiments could place the surgical robotic system into the PAUSED 59 mode. When the user is ready to resume teleoperation, it may be the case that the UID no longer matches the frozen position of the surgical robotic grasper, as the UID may have been set aside, moved, opened or closed, etc. The state diagram in FIG. 5B shows how the UID can be again matched to the surgical robotic grasper, so that teleoperation can be resumed from the PAUSED 59 mode. Two possibilities are expressly accounted for in the state diagram. One possibility is that the system is paused with robotic grasper force $>F_{min}$ (value 71), e.g., the surgical robotic grasper 30 is clamping on tissue. Another possibility is that the system is paused with robotic grasper force $<F_{min}$ (value 73), e.g., the robotic grasper is open and not clamping on anything.

The teleoperation mode of PAUSED 59 directs a transition from the unmatching/match algorithm state of MATCHING 65 to the state of MATCHED 67 according to the value of the robotic grasper force. If the system has been paused while the robotic grasper force is greater than a threshold, Fmin, then the transition from MATCHING 65 to MATCHED 67 may occur in response to the UID grasper 22 closing (from being open.) This is so that the surgical robotic grasper force is more readily maintained, clamping on tissue, as the UID approaches and matches the angle of the surgical robotic grasper. Under this condition, the user is expected to open the UID grasper 22, then (e.g., gradually) close the UID grasper 22 until the user input from the UID 14 matches the surgical robotic grasper, at which point the system can indicate matched and therefore resume teleoperation (at which point the user input from the UID gets mapped to the surgical robotic grasper).

If however the system was paused when the robotic grasper force was less than the minimum threshold Fmin (e.g., essentially zero and where the grasper 30 is open and not clamping anything), then the transition from MATCHING 65 to MATCHED 67 may occur either when the UID grasper 22 is opening (from being closed) or when the UID grasper 22 closes some (from being open). This depends on how large the match threshold is and on the values (e.g., angles) of the robotic grasper variable and the UID variable. For instance, if the robotic grasper is halfway open and the UID grasper is full open, the user is expected to close the UID grasper some in order to match (unless the match threshold was one-half of the full range). If the robot grasper is halfway open and the UID grasper is full closed, the user is expected to open the UID grasper some in order to match.

Upon entering the MATCHED 67 state, the algorithm will indicate that the ENGAGED 60 teleoperation mode may be resumed. In this manner, the surgical robotic grasper force is less likely to suddenly increase, which might damage patient tissue or equipment, as the UID approaches and matches the surgical robotic grasper.

With reference to FIG. 5A, to go from the DISENGAGED 57 to ENGAGED 60 teleoperation mode, the unmatch/ match algorithm state is initialized as UNMATCHING_ OPEN 61, and then passes through the following sequence of {UMMATCHING_CLOSE 62, MATCHING 65, MATCHED 67}. The UNMATCHING_OPEN 61 and UNMATCHING_CLOSE 62 states require the UID grasper to cover a full range of open to closed, thus ensuring that a mismatch between the UID grasper 22 and surgical robotic grasper 30 initially always occurs. This is because when the system is disengaged, the surgical robotic grasper 30 is not being controlled to follow the UID 14, and there is no guarantee that the UID matches the surgical robotic grasper. Even the slightest manipulation of the UID grasper 22, while the system is paused or disengaged, will result in a mismatch (no match) between the UID and the surgical robotic grasper. To re-engage teleoperation from the DISENGAGED 57 mode, the user is expected to open the UID grasper 22 (e.g., release and rely on a spring-loaded mechanism to self-open), then close the UID grasper 22, then open the UID grasper 22 until the user input from the UID 14 matches the sensed angle and/or force of the surgical robotic grasper 30. This provides a consistent set of required user inputs regardless of the initial values of the user inputs and the initial values of the angle and force of surgical robotic grasper 30, thus creating a simple user interface that requires minimal training and no guess work.

Once unmatch is complete, the state transitions to MATCHING 65 and the algorithm waits for the UID to match the surgical robotic grasper 30 before finally transitioning to the MATCHED 67 state. Once in the MATCHED 67 state, teleoperation can be engaged, with the teleoperation mode ENGAGED 60. The UID actions to perform unmatch may be chosen to be open and then closed (and not vice versa) so that the matching typically occurs in the opening direction (e.g., release) of the UID grasper 22 and thus is less likely to result in the user unintentionally applying high grasper forces to the tissue. Matching is allowed to occur in the closing direction (e.g., squeeze), for the case where the robotic grasper is applying large forces while tightly grasping tissue. This behavior is desirable because matching the UID to the surgical robotic grasper 30 in the opening direction would result in the user unintentionally dropping the grasped tissue.

The robotic grasper range, expressed in units of pressure, for which matching can occur in the closing direction, can be determined from the algorithm parameters as $\tilde{g}_u >  g_{u,closed} - \delta g_{match} + g_{u,noise}$. The parameter $g_{u,noise}$ is some small value greater than 0, which can be determined by the noise characteristics of the sensor, as the closed threshold $g_{u,closed}$ might not be crossed at a UID value of exactly $g_{u,closed}$.

In contrast to the case where the system is disengaged from teleoperation, consider the case where the system is paused (and so enters the PAUSED 59 mode). There, the algorithm waits for the UID to "re-match" the last, retained robot grasper value (corresponding to the robotic grasper being held or frozen by the control system when paused), because upon being PAUSED, the robot grasper is automatically held in its last pose. To go from the PAUSED 59 to ENGAGED 60 teleoperation mode, the algorithm state is initialized as MATCHING 65 and waits for the UID 22 to match the surgical robotic grasper 30 in order to transition to the MATCHED 67 state allowing teleoperation to be engaged (see FIG. 5B). It is assumed that in the paused teleoperation mode, the user is alert and accidental engagement will not occur.

1) Alternative embodiment for translating from surgical robotic grasper value to corresponding units of the UID:

The mapping from surgical robotic grasper $g_r=[\theta_g, f_g]$ to corresponding units of the UID $\tilde{g}_r$ described in the previous section can result in a different range of the UID values being mapped to surgical robotic grasper angle 33 (see FIG. 2B) and force for different instruments (see FIGS. 4A and 4B). It may be desirable to have the UID range translated to surgical robotic grasper angle 33, and the UID range translated to surgical robotic grasper force, be consistent across different surgical instruments. In this case, the inverse translation $\tilde{g}_r = f^{-1}(g_r)$ would be as given below.

$$\bar{\theta}_g = \{\max(\theta_{g,min}, \min(\theta_g, \theta_{g,max}))\},$$

$$f_g \le \varepsilon_f \min\left(\left(\frac{f_g}{k_{angle\_to\_force}}, \frac{f_{g,max}}{k_{angle\_to\_force}}\right)\right), f_g > \varepsilon_f$$

$$\alpha = \left\{-\left(\frac{g_{u,zero} - g_{u,min}}{\theta_{g,max} - \theta_{g,min}}\right), \bar{\theta}_g \ge 0 - \left(\frac{g_{u,zero} - g_{u,max}}{\frac{f_{g,max}}{k_{angle\_to\_force}}}\right), \bar{\theta}_g < 0\right.$$

$$\tilde{g}_r = \left\{g_{u,min} + \alpha(\bar{\theta}_g - \theta_{g,max}), \bar{\theta}_g \ge 0 \; g_{u,max} + \alpha\left(\bar{\theta}_g - \frac{f_{g,max}}{k_{angle\_to\_force}}\right), \bar{\theta}_g < 0\right.$$

The parameter a $g_{u,zero}$ is the UID pressure value equivalent to the surgical robotic grasper being at minimum gripper angle and zero force.

2) Alternative embodiment for estimating the surgical robotic grasper value in UID units:

Two different methods for mapping from surgical robotic grasper $g_r=[\theta_g, f_g]$ to corresponding units of the UID $\tilde{g}_r$ were proposed. However, given difficulty in accurately estimating the grasper force, an additional alternative embodiment can be used. During teleoperation (ENGAGED 80 mode), the surgical robotic grasper 30 is commanded to follow the UID $g_u$ according to the translation function $g_r = f(g_u)$. Assuming reasonable tracking performance, the surgical robotic grasper will be very close to the commanded surgical robotic grasper variable, which is computed from the UID $g_u$. Thus, the surgical robotic grasper in corresponding UID units $\tilde{g}_r$ will be very close to the UID $g_u$ whenever teleoperation is active (i.e. in the ENGAGED 60 mode). When teleoperation transitions from ENGAGED 60 to either the PAUSED 59 or DISENGAGED 57 modes, teleoperation is inactive and the surgical robotic grasper 30 will be held at the last commanded pose. Given that the surgical robotic grasper 30 only changes pose when teleoperation is active (in the ENGAGED 60 mode) and provided that the surgical robotic grasper 30 adequately tracks the command, the surgical robotic grasper (in corresponding UID units) $\tilde{g}_r$ can be set to the UID $g_u$ whenever teleoperation is active (ENGAGED 60). When teleoperation is inactive (changes to either DISENGAGED 57 or PAUSED 59), $\tilde{g}_r$ will be latched to the last value of $g_u$ in ENGAGED 60.

Figure 6A:
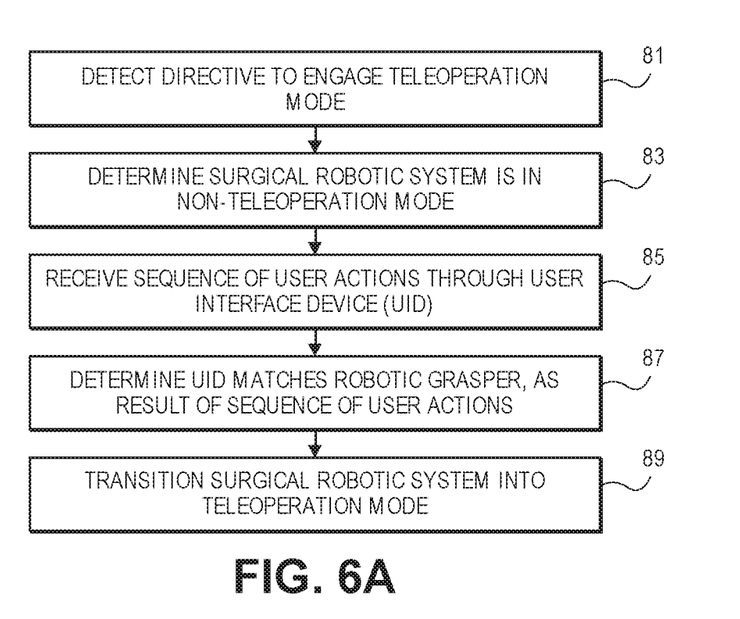
FIG. 6A is a flow diagram of a method for engaging teleoperation of a surgical robotic system.

FIG. 6A is a flow diagram of a method for engaging teleoperation of a surgical robotic system, which can be practiced on or by embodiments.

In an action 81, the surgical robotic system detects a directive to engage teleoperation mode. For example, the system could detect that i) the UID is picked up by a user or otherwise removed from its dock of the system, ii) a user gaze is focused on a display of a user console of the system, or iii) pedal action occurs at foot pedals of the system. These or other detected actions or events are interpreted by the system as a directive to engage teleoperation. In one embodiment, the detected actions or events are part of a clutch release process which shows the user's intent to un-pause the system (resume teleoperation).

In an action 83, the system determines that it is in a non-teleoperation mode. For example, the system could be in a disengaged mode. The system could alternatively be in a paused mode. In both modes, the UID is prevented from controlling the robotic grasper. However, in the disengaged mode an elaborate process or series of checks need to be performed by the system in order to permit the unmatch/match algorithm to re-engage in teleoperation. In contrast, in the paused mode, the system performs a simple process to permit re-engaging in teleoperation, e.g., detect that the user has "released" the clutch.

In an action 85, the system has been directed to re-engage teleoperation, and receives a sequence of detected user actions through a user interface device (UID). In one version, the sequence of user actions includes opening the UID, closing the UID, and then again opening the UID until the system detects that the UID and the robotic grasper match as a result of the sequence of user actions (action 87). Next, in an action 89, in response to the match detected in action 87, the surgical robotic system is transitioned into teleoperation mode.

To extend the above method, one embodiment of the surgical robotic system provides guidance on the sequence of user actions. For example, the system could display instructions, diagrams or images on the display on the user console, give audio instructions, sequence a series of lighted arrows on the UID, or otherwise give visual, audio or tactile guidance to the user on how to produce the sequence of user actions. In another extension of the above method, one embodiment of the surgical robotic system displays an indication of the transitioning into teleoperation mode. For example, the system could produce an audible alert, display a message, diagram or image on the display on the user console, activate a light or otherwise display an indication to the user that teleoperation is being engaged.

Figure 6B:
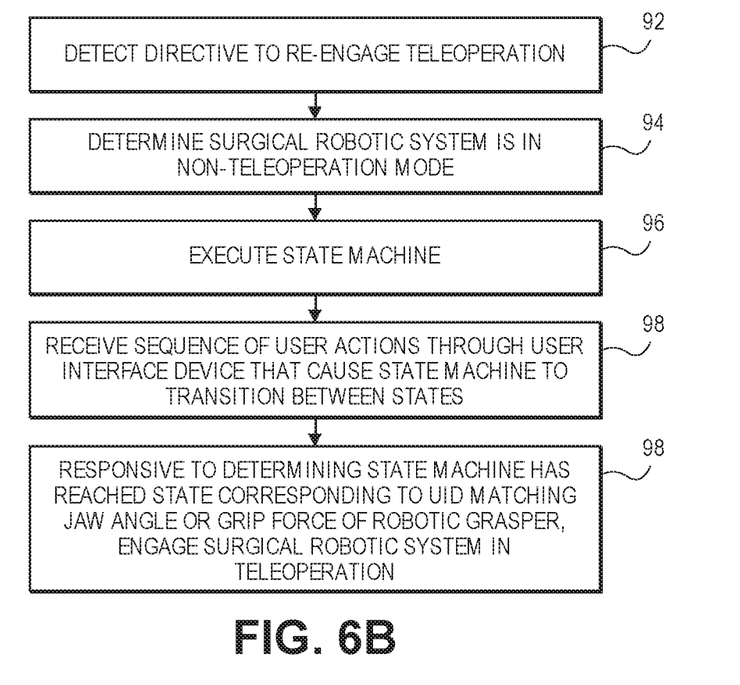
FIG. 6B is a flow diagram of another method of engaging teleoperation of a surgical robotic system.

FIG. 6B is a flow diagram of a method for re-engaging teleoperation for a surgical robotic system, which can be practiced on or by embodiments. In an action 92, the surgical robotic system detects a directive to re-engage teleoperation. For example, the system could detect that the UID is picked up or otherwise removed from a dock of the system, a user gaze is focused on a display of a user console of the system, or pedal action occurs at foot pedals of the system. These or other detected actions or events are interpreted by the system as a directive to re-engage teleoperation.

In an action 94, the system determines that it is in a non-teleoperation mode.

In an action 96, the system executes a state machine. In one version, the state machine has a matching state for waiting for the UID to match the robotic grasper, and a matched state for when the UID matches the robotic grasper. The system transitions from the matching state, for waiting for the UID to match the robotic grasper, to the matched state, for when the UID matches the robotic grasper, in response to the UID matching the robotic grasper. The system engages teleoperation when in the matched state.

In another version, the state machine has an unmatching open state during which it waits for the UID grasper to sufficiently open, before transitioning into an unmatching close state during which it waits for the UID grasper to sufficiently close, before transitioning into the matching state.

In an action 98, the system receives a sequence of user actions through a user interface device (UID). This sequence of user actions causes the state machine to transition between states. In one version, the sequence of user actions includes opening the UID, and closing the UID until the UID and the robotic grasper match.

In an action 99, responsive to determining that the state machine has reached a state corresponding to the UID matching a jaw angle or grip force of a robotic grasper of the surgical robotic system, the surgical robotic system engages the UID and robotic grasper in teleoperation.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, while FIGS. 2A and 2B depict a particular example of the UID grasper 22 and the surgical robotic grasper 30, other UIDs, graspers and tools are possible. The UID grasper 22 may be part of the UID 14 which as shown in the example of FIG. 1 is an ungrounded device—it is not mechanically linked to a base or frame; alternatively, the UID grasper 22 may be part of a UID 14 that is grounded, i.e., mechanically linked to a base or frame. The description is thus to be regarded as illustrative instead of limiting.

What is claimed is:

1. A surgical robotic system comprising:
   a robotic grasper having two jaws;
   a user interface device (UID); and
   one or more processors communicatively coupled to the UID and the robotic grasper and configured to control operation of the robotic grasper in accordance with user input from the UID while teleoperation mode is engaged, prevent the UID from controlling the robotic grasper while the system is in a non-teleoperation mode, and perform the following operations while the system is in the non-teleoperation mode:
   detect a directive to engage or re-engage the teleoperation mode;
   receive a sequence of detected user actions through the UID;
   determine that, as a result of the sequence of detected user actions, the UID matches a jaw angle between the two jaws or a grip force affected by the two jaws of the robotic grasper; and
   transition the surgical robotic system into the teleoperation mode, responsive to determination that the UID matches the jaw angle or the grip force.

2. The surgical robotic system of claim 1, wherein the directive to engage or re-engage the teleoperation mode is indicated by at least one of the UID being removed from a dock by a user, focusing of a user gaze on a display of a user console, or a pedal action by a user.

3. The surgical robotic system of claim 1, wherein:
   the non-teleoperation mode includes one of disengaged mode or pause mode;
   wherein the disengaged mode is with the UID disengaged from controlling the robotic grasper, prior to a teleoperation session; and
   the pause mode is with the UID disengaged from controlling the robotic grasper to pause a teleoperation session.

4. The surgical robotic system of claim 1, wherein the sequence of detected user actions includes opening the UID, closing the UID, and opening the UID until the UID and the robotic grasper match.

5. The surgical robotic system of claim 1, wherein to determine the UID matches and to transition the surgical robotic system into the teleoperation mode, the one or more processors are further configured to operate a state machine comprising:
   an unmatching open state for waiting for the UID to open, transitioning to an unmatching close state when the UID is open and starts to close;
   the unmatching close state for waiting for the UID to close, transitioning to a matching state when the UID is closed and starts to open;
   the matching state for waiting for the UID to match the robotic grasper, transitioning to a matched state when the UID matches the robotic grasper; and
   the matched state for when the UID matches the robotic grasper, and for the transition into the teleoperation mode.

6. The surgical robotic system of claim 1, wherein the one or more processors are further configured to:
   determine that the surgical robotic system is in a pause mode;
   receive a user action to match the UID and the robotic grasper; and
   transition the surgical robotic system into the teleoperation mode.

7. The surgical robotic system of claim 1, wherein the one or more processors are further configured to:
   provide a guidance on the sequence of detected user actions.

8. The surgical robotic system of claim 1, wherein the one or more processors are further configured to:
   display an indication of a match state, responsive to determining the UID matches the jaw angle or the grip force.

9. A method of re-engaging teleoperation for a surgical robotic system, the method comprising the following operations while the system is in a non-teleoperation mode, wherein in the non-teleoperation mode, a robotic grasper is not being controlled by the system to follow a user interface device, UID, of the system:
   detecting, by one or more processors communicatively coupled to the UID and to the robotic grasper, a directive to re-engage teleoperation;
   executing, by the one or more processors, a state machine having a plurality of states;
   receiving a sequence of user actions through the UID that cause the state machine to transition between the plurality of states; and
   responsive to determining that the state machine has reached a state corresponding to the UID matching a jaw angle or a grip force of the robotic grasper, engaging the surgical robotic system in teleoperation.

10. The method of claim 9, wherein the plurality of states comprises a matching state for waiting for the UID to match the robotic grasper.

11. The method of claim 9, wherein the plurality of states comprises a matched state for when the UID matches the robotic grasper.

12. The method of claim 9, wherein the executing the state machine comprises transitioning from a first state for waiting for the UID to match the robotic grasper to a second state for when the UID matches the robotic grasper, responsive to the UID matching the robotic grasper.

13. The method of claim 12, wherein the sequence of user actions that result in transitioning from the first state to the second state are when the user is squeezing a UID grasper linkage or deformable surface.

14. A method for engaging teleoperation of a surgical robotic system, performed by the surgical robotic system, the method comprising the following operations while the surgical robotic system is not in a teleoperation mode, wherein in the teleoperation mode, a robotic end effector is controlled by user inputs received from a user input device (UID):
   detecting a directive to engage the teleoperation mode;
   receiving a sequence of user actions through the UID;
   determining that, as a result of the sequence of user actions, the UID matches a position of, or a grip force affected by, the robotic end effector; and
   transitioning the surgical robotic system into the teleoperation mode, as a result of the determining the UID matches the position or the grip force of the robotic end effector.

15. The method of claim 14, wherein the detecting the directive to engage or re-engage the teleoperation mode comprises detecting at least one of a clutch release by a user, the UID being removed from a dock, focusing of a user gaze on a display of a user console, or pedal action.

16. The method of claim 14, wherein:
   the surgical robotic system not in the teleoperation mode includes one of disengaged mode or pause mode;
   the disengaged mode is when the system performs an elaborate process before enabling teleoperation; and
   the pause mode is when the system performs a simple process before enabling teleoperation.

17. The method of claim 14, wherein the sequence of user actions includes opening the UID, closing the UID, and opening the UID until the UID and the robotic end effector match.

18. The method of claim 14, further comprising:
   receiving a user action to match the UID and the robotic end effector, while the surgical robotic system is in a pause mode; and then
   transitioning the surgical robotic system from the pause mode into the teleoperation mode.

19. The method of claim 14, further comprising:
   providing a guidance on the sequence of user actions.

20. The method of claim 14, further comprising:
   displaying an indication of the transitioning the surgical robotic system into the teleoperation mode.

* * * * *